United States Patent
Fell (10) Patent No.: US 7,491,235 B2
(45) Date of Patent: Feb. 17, 2009

(54) SURGICALLY IMPLANTABLE KNEE PROSTHESIS

(76) Inventor: Barry M. Fell, 7124 Red Top Rd., Hummelstown, PA (US) 17036

( * ) Notice: Subject to any disclaimer, the term of this patent is extended or adjusted under 35 U.S.C. 154(b) by 226 days.

(21) Appl. No.: 10/832,213

(22) Filed: Apr. 26, 2004

(65) Prior Publication Data

US 2004/0199250 A1   Oct. 7, 2004

(51) Int. Cl.
*A61F 2/08* (2006.01)
(52) U.S. Cl. .............. 623/14.12; 623/20.14; 623/20.3
(58) Field of Classification Search ............ 623/14.12, 623/20.14–20.31
See application file for complete search history.

(56) References Cited

U.S. PATENT DOCUMENTS

| 3,869,731 A | 3/1975 | Waugh et al. |
| 4,085,466 A | 4/1978 | Goodfellow et al. |
| 4,207,627 A | 6/1980 | Cloutier |
| 4,224,696 A | 9/1980 | Murray et al. |
| 4,257,129 A | 3/1981 | Volz |
| 4,340,978 A | 7/1982 | Buechel et al. |
| 4,344,193 A | 8/1982 | Kenny |
| 4,385,404 A | 5/1983 | Sully et al. |
| 4,446,578 A | 5/1984 | Perkins et al. |
| 4,502,161 A | 3/1985 | Wall |
| 4,759,767 A | 7/1988 | Lacey |
| 4,808,185 A | 2/1989 | Penenberg et al. |
| 4,822,362 A | 4/1989 | Walker et al. |
| 4,865,607 A | 9/1989 | Witzel et al. |
| 4,883,488 A | 11/1989 | Bloebaum et al. |
| 4,919,667 A | 4/1990 | Richmond |
| 4,936,853 A | 6/1990 | Fabian et al. |
| 5,007,934 A | 4/1991 | Stone |
| 5,067,964 A | 11/1991 | Richmond et al. |
| 5,137,536 A | 8/1992 | Koshino |
| 5,171,283 A | 12/1992 | Pappas et al. |
| 5,171,322 A | 12/1992 | Kenny |
| 5,176,710 A | 1/1993 | Hahn et al. |
| 5,271,737 A | 12/1993 | Baldwin et al. |
| 5,282,868 A | 2/1994 | Bahler |

(Continued)

FOREIGN PATENT DOCUMENTS

DE       3840470       6/1990

(Continued)

OTHER PUBLICATIONS

Wheeler, John, "Little Device Could Pack a Big Punch," Sulzer Medica Journal Feb. 2000, pp. 16-17.

*Primary Examiner*—Dave Willse
*Assistant Examiner*—Javier G Blanco
(74) *Attorney, Agent, or Firm*—Brooks Kushman P.C.

(57) ABSTRACT

A prosthesis is provided for implantation into a body joint, such as a knee joint compartment between a femoral condyle and its corresponding tibial plateau, without requiring bone resection. The prosthesis includes a body having a generally elliptical shape in plan and including opposed top and bottom surfaces. The body includes a supporting portion and a coating portion, where the supporting portion has at least one surface at least partially disposed within an interior of the body and the coating portion has at least one surface disposed on an exterior of the body. The supporting portion is constructed from a higher modulus material than the coating portion such that the body is at least slightly deformable.

30 Claims, 4 Drawing Sheets

U.S. PATENT DOCUMENTS

| | | | |
|---|---|---|---|
| 5,336,266 A | 8/1994 | Caspari et al. | |
| 5,358,530 A | 10/1994 | Hodorek | |
| 5,358,531 A | 10/1994 | Goodfellow et al. | |
| 5,387,240 A | 2/1995 | Pottenger et al. | |
| 5,395,376 A | 3/1995 | Caspari et al. | |
| 5,395,401 A | 3/1995 | Bahler | |
| 5,405,396 A | 4/1995 | Heldreth et al. | |
| 5,658,342 A | 8/1997 | Draganich et al. | |
| 5,683,468 A | 11/1997 | Pappas | |
| 5,702,466 A | 12/1997 | Pappas et al. | |
| 5,725,584 A | 3/1998 | Walker et al. | |
| 5,776,200 A | 7/1998 | Johnson et al. | |
| 5,782,925 A | 7/1998 | Collazo et al. | |
| 5,871,541 A | 2/1999 | Gerber | |
| 5,871,542 A | 2/1999 | Goodfellow et al. | |
| 5,871,543 A | 2/1999 | Hofmann | |
| 5,871,545 A | 2/1999 | Goodfellow et al. | |
| 5,879,387 A | 3/1999 | Jones et al. | |
| 5,879,394 A | 3/1999 | Ashby et al. | |
| 5,944,759 A * | 8/1999 | Link | 623/18.11 |
| 5,957,979 A | 9/1999 | Beckman et al. | |
| 5,964,808 A | 10/1999 | Blaha et al. | |
| 6,013,103 A | 1/2000 | Kaufman et al. | |
| 6,090,144 A | 7/2000 | Letot et al. | |
| 6,123,728 A | 9/2000 | Brosnahan et al. | |
| 6,165,223 A | 12/2000 | Metzger et al. | |
| 6,206,927 B1 | 3/2001 | Fell et al. | |
| 6,210,444 B1 | 4/2001 | Webster et al. | |
| 6,245,110 B1 | 6/2001 | Grundei et al. | |
| 6,258,126 B1 | 7/2001 | Colleran | |
| 6,258,127 B1 | 7/2001 | Schmotzer | |
| 6,299,645 B1 | 10/2001 | Ogden | |
| 6,413,279 B1 | 7/2002 | Metzger et al. | |
| 6,428,577 B1 | 8/2002 | Evans et al. | |
| 6,558,421 B1 | 5/2003 | Fell et al. | |
| 6,629,997 B2 | 10/2003 | Mansmann | |
| 6,660,039 B1 | 12/2003 | Evans et al. | |
| 6,679,914 B1 | 1/2004 | Gabbay | |
| 6,726,724 B2 | 4/2004 | Repicci | |
| 6,855,165 B2 | 2/2005 | Fell et al. | |
| 6,866,684 B2 | 3/2005 | Fell et al. | |
| 6,893,463 B2 | 5/2005 | Fell et al. | |
| 6,911,044 B2 | 6/2005 | Fell et al. | |
| 6,923,831 B2 | 8/2005 | Fell et al. | |
| 2002/0055784 A1 * | 5/2002 | Burstein et al. | 623/20.28 |
| 2002/0173855 A1 | 11/2002 | Mansmann | |
| 2003/0060884 A1 | 3/2003 | Fell et al. | |
| 2003/0060888 A1 | 3/2003 | Fell et al. | |
| 2004/0006393 A1 | 1/2004 | Burkinshaw | |
| 2004/0006394 A1 | 1/2004 | Lipman et al. | |
| 2004/0133275 A1 | 7/2004 | Mansmann | |
| 2004/0153163 A1 | 8/2004 | Posner | |
| 2004/0199249 A1 | 10/2004 | Fell | |
| 2004/0220677 A1 | 11/2004 | Delfosse et al. | |
| 2004/0267363 A1 | 12/2004 | Fell et al. | |
| 2005/0033424 A1 | 2/2005 | Fell | |
| 2005/0171604 A1 | 8/2005 | Michalow | |
| 2005/0209703 A1 | 9/2005 | Fell | |

FOREIGN PATENT DOCUMENTS

| | | |
|---|---|---|
| EP | 1 095 638 A2 | 5/2001 |
| FR | 2635678 | 3/1990 |
| FR | 2700263 | 7/1994 |
| FR | 2747914 | 10/1997 |
| GB | 2278782 A | 12/1994 |
| GB | 2302282 A | 1/1997 |
| GB | 2312166 A | 10/1997 |
| WO | WO 95/27450 | 10/1995 |

* cited by examiner

SURGICALLY IMPLANTABLE KNEE PROSTHESIS

BACKGROUND OF THE INVENTION

1. Field of the Invention

The present invention pertains to a prosthetic device which is surgically implantable into a body joint, and more particularly to a knee joint prosthesis which may be surgically implanted between the femoral condyle and tibial plateau of the knee compartment.

2. Background Art

Articular cartilage and meniscal cartilage provide the mobile weight bearing surfaces of the knee joint. Damage to these surfaces is generally due to genetic predisposition, trauma, and/or aging. The result is usually the development of chondromalacia, thinning and softening of the articular cartilage, and degenerative tearing of the meniscal cartilage. Various methods of treatment are available to treat these disease processes. Each option usually has specific indications and is accompanied by a list of benefits and deficiencies that may be compared to other options.

The healthy knee joint has a balanced amount of joint cartilage across the four surfaces of this bicompartmental joint (medial femoral condyle, medial tibial plateau, lateral femoral condyle, and lateral tibial plateau). In patients with osteoarthritis, the degenerative process typically leads to an asymmetric wear pattern that leaves one compartment with significantly less articular cartilage covering the weight bearing areas of the tibia and femur than the other compartment. Most commonly, the medial compartment of the knee joint is affected more often than the lateral compartment.

As the disease progresses, large amounts of articular cartilage are worn away. Due to the asymmetric nature of the erosion, the alignment of the mechanical axis of rotation of the femur relative to the tibia becomes tilted down towards the compartment which is suffering the majority of the erosion. The result is a varus (bow-legged) deformity in the case of a medial compartment disease predominance, or a valgus (knock-kneed) deformity in the case of lateral compartment disease predominance. Factors such as excessive body weight, previous traumatic injury, knee instability, the absence of the meniscus, and genetic predisposition all affect the rate of the disease.

Osteoarthritis is usually defined in stages of Grade I through V, with Grade III revealing significant articular cartilage loss, Grade IV revealing some eburnation of the subchondral bone, and Grade V detailing both significant articular loss and bone loss. The disease manifests itself as periodic to continuous pain that can be quite uncomfortable for the patient. The cause of this pain is subject to many opinions but it is apparent that, as the joint compartment collapses, the collateral ligament on the side of the predominant disease becomes increasingly slack and the tibial and femoral axes move, for example, from a varus to a valgus condition. This increases the stress on the opposing collateral ligament as well as the cruciate ligaments, and shifts the load bearing function of this bicompartmental joint increasingly towards the diseased side. This increasing joint laxity is suspected of causing some of the pain one feels. In addition, as the bearing loads are shifted, the body responds to the increased loading on the diseased compartment with an increased production of bony surface area (osteophytes) in an attempt to reduce the area unit loading. All of this shifting of the knee component geometry causes a misalignment of the mechanical axis of the joint. This misalignment causes an increase in the rate of degenerative change to the diseased joint surfaces, causing an ever-increasing amount of cartilage debris to build up in the joint, and further causing joint inflammation and subsequent pain.

Currently, there is a void in options used to treat the relatively young patient with moderate to severe chondromalacia involving mainly one compartment of the knee. Current treatments include NSAIDS, cortisone injections, hyaluronic acid (HA) injections, and arthroscopic debridement. Some patients cannot tolerate or do not want the risk of potential side effects of NSAIDS. Repeated cortisone injections actually weaken articular cartilage after a long period of time. HA has shown promising results, but is only a short term solution for pain. Arthroscopic debridement alone frequently does not provide long lasting relief of symptoms.

Unfortunately, the lack of long term success of these treatments leads to more invasive treatment methods. Osteochondral allografts and microfracture techniques are indicated for small cartilage defects that are typically the result of trauma. These procedures are not suitable for addressing large areas of degeneration. In addition, osteochondral allografts can only be used to address defects on the femoral condyle, as tibial degeneration cannot be addressed with this technique. High tibial osteotomy (HTO) corrects the varus malalignment between the tibia and the femur but, because it is performed below the joint line, it does not fill the cartilage void or re-tension the medial collateral ligament (MCL). Removing bone and changing the joint line does not complicate the conversion to total knee arthroscopy (TKA). However, an HTO does leave a hard sclerotic region of bone which is difficult to penetrate, making conversion to a total knee replacement (TKR) technically challenging. Unicompartmental and bicompartmental total knee replacements resect significant amounts of bone and, if performed on younger patients, will likely require revision surgery as they age. Revision total knee replacement surgery is usually extensive and results in predictably diminished mechanical life expectancy. Therefore, it is best to delay this type of bone resecting surgery as long as possible.

The only true solution is to rebuild the defective joint by "filling" the joint space with more articular bearing material through a complete resurfacing of the existing femoral condyle and tibial plateau. By replacing the original cartilage to its pre-diseased depth, the joint mechanical axis alignment is restored to its original condition. Unfortunately, these natural articular materials and surgical technology required to accomplish this replacement task do not yet exist.

Currently, replacement of the existing surfaces, with materials other than articular cartilage, is only possible with a total or uni-condylar knee replacement, and these procedures require removal of significant amounts of the underlying bone structure. The alternative method is to fill the joint space with a spacer that replaces the missing articular materials.

Attaching a new bearing surface to the femoral condyle is technically challenging and was first attempted, with limited success, over 40 years ago with the MGH (Massachusetts General Hospital) knee. Like a dental crown, it covered both the femoral condyles with Vitallium (CoCr) and would bear against the existing tibial plateau. Tibial covering devices such as the McKeever, Macintosh, and Townley tibial tray maintained the existing femoral surface as the bearing surface but, like the MGH knee, all required significant bone resection, thus making them less than ideal solutions as well. These devices also made no particular attempt to match the patient's specific femoral or tibial geometry, thus reducing their chances for optimal success. Because these devices were made of CoCr, which has different viscoelastic and wear properties from the natural articular materials, any surface geometry which did not closely match the bearing surface of the tibia or femur could cause premature wear of the remaining cartilage due to asymmetric loading.

Newer materials technologies in development including filling the joint space by injecting polyurethane (U.S. Pat. No. 5,795,353) into the joint and anchoring it with holes drilled into the tibial plateau. Others include a series of polymeric materials such as PVA hydrogels in a titanium mesh (see Chang et al, *Journal of Biomedical Materials Research* 37, 51-59, 1997), biodegradable anhydride prepolymers that can be cross-linked with irradiation by UV light (U.S. Pat. No. 5,902,599), and in vivo grown articular chondrocytes in a collagen fiber or other biocompatible scaffold (U.S. Pat. No. 5,158,574). Other low surface energy materials, such as low temperature isotropic (LTI) pyrolitic carbon, have been investigated as bearing surfaces as well. However, these techniques are limited by one's ability to first of all fashion these materials in a conformal manner to replicate the existing knee geometry, while at the same time maintaining their location within the joint, while further being able to survive the mechanical loading conditions of the knee.

U.S. Pat. Nos. 6,206,927 and 6,558,421 and copending U.S. application Ser. No. 10/232,608, each of which are incorporated by reference herein, disclose a prosthesis for the knee compartment which fills the joint space in order to replace the missing articular materials. This prosthesis provides an anatomically correct bearing surface for both the tibial plateau and femoral condyle to articulate against. Additionally, the prosthesis reduces the concentrated loads on the femoral condyle and its articular cartilage and maintains proper spatial location of the femoral condyle to the tibial plateau, thereby restoring normal joint alignment. Advantageously, the prosthesis does not require any bone resection or any means of bone fixation.

In addition to these benefits, it is also desired to provide a unicompartmental prosthesis which has improved load absorbing characteristics, provides improved load carrying ability throughout the complete range of motion (ROM), and increases patient comfort and device longevity.

SUMMARY OF THE INVENTION

Accordingly, a prosthesis is provided for implantation into a body joint, such as the knee joint compartment between a femoral condyle and its corresponding tibial plateau, without requiring bone resection. The prosthesis includes a body having a generally elliptical shape in plan and including opposed top and bottom surfaces. The body includes a supporting portion and a coating portion, where the supporting portion has at least one surface at least partially disposed within an interior of the body and the coating portion has at least one surface disposed on an exterior of the body. The supporting portion is constructed from a higher modulus material than the coating portion such that the body is at least slightly deformable.

The coating portion includes a top layer disposed on an upper surface of the supporting portion, or a bottom layer disposed on a lower surface of the supporting portion, or both. Typically, the top layer is on average of greater thickness than the bottom layer. The top layer can have constant or variable thickness, as can the bottom layer. When a bottom layer is utilized, it preferably has a thickness of about 0.1 to 1.0 mm. The coating portion can cover part or all of the surfaces of the supporting portion, or can be configured to surround the supporting portion. The coating portion could be joined to the supporting portion by overmolding the coating portion onto the supporting portion, or could be joined to the supporting portion by surface treatment of the supporting portion. The supporting portion can be solid, or alternatively can have a porous configuration, such as a lattice. Depending upon the requirements of the implantation site, the upper surface of the supporting portion can be generally flat, generally concave, or generally convex. Typically, the lower surface of the supporting portion is either generally flat or generally concave.

In a preferred embodiment, the coating portion is constructed at least partially from a material selected from the group consisting of hydrogels, reinforced and non-reinforced elastomeric polymers, thermoplastic urethanes, hyaluronan derivatives or composites, viscous-elastic materials, or composites thereof. Hydrogels can include polyacrylic acid (PAA) hydrogels, photo-crosslinked polyethylene oxide (PEO) hydrogels, polyvinyl pyrrolidone (PVP) hydrogels, and PVA based hydrogels. The supporting portion is preferably constructed at least partially of a material selected from the group consisting of ceramics, metals, metal alloys, hydrogels, reinforced and non-reinforced thermoset or thermoplastic polymers, or composites thereof. The body can be constructed at least partially of a material capable of containing living cells, and can have an active material associated therewith. Furthermore, a surface application associated with the coating portion, such as for the reduction of friction.

Depending upon the implantation site, the top surface of the body is typically generally concave or generally convex, and the bottom surface of the body is typically generally flat or generally concave. A peripheral edge extends between the top and bottom surfaces of the body and having a first side, a second side opposite the first side, a first end, and a second end opposite the first end. In a preferred embodiment, a first dimension D is defined by the first end and the second end, and a second dimension F is defined by the first side and the second side, where the dimension F is from about 0.25D to about 1.5D. Preferably, outside edges along a periphery of the body are rounded. The body can be free of any means of fixation within the knee joint compartment, or alternatively can be arranged to be constrained within the knee joint compartment.

Corresponding, a method is provided for implantation of a prosthesis into a knee joint compartment between a femoral condyle and its corresponding tibial plateau without requiring bone resection. The method includes providing a prosthesis including a body having a generally elliptical shape in plan and opposed top and bottom surfaces, the body including a supporting portion and a coating portion, the supporting portion having at least one surface at least partially disposed within an interior of the body and the coating portion having at least one surface disposed on an exterior of the body, where the supporting portion is constructed from a higher modulus material than the coating portion such that the body is at least slightly deformable. The method further includes surgically exposing the knee joint compartment, and inserting the prosthesis into the knee joint compartment.

In further accordance with the present invention, the method can include determining a size and shape of the prosthesis required by examination of the knee joint, where the examination may include one or more of X-ray imaging and MRI imaging. The method can include selecting the prosthesis from a library of prostheses of standard shapes and sizes, or alternatively generating a custom prosthesis whose size and shape are at least partially based on the examination of the knee joint. The method can also include altering the condition of tissue located in the knee joint compartment or adjacent thereto.

In a preferred embodiment, the method includes pre-loading the prosthesis during implantation. Depending upon the materials utilized, the method may further include hydrating at least part of the prosthesis during implantation. Still further, the method according to the present invention can include providing an active material associated with the prosthesis, or modifying surface properties of the coating portion.

According to the present invention, a method is provided for correcting misalignment in an axis of rotation of a knee joint. The method includes providing a prosthesis including a body having a generally elliptical shape in plan and opposed top and bottom surfaces, the body including a supporting portion and a coating portion, the supporting portion having at least one surface at least partially disposed within an interior of the body and the coating portion having at least one surface disposed on an exterior of the body, where the supporting portion is constructed from a higher modulus material than the coating portion such that the body is at least slightly deformable. The method further includes surgically exposing the knee joint, and inserting the prosthesis into the knee joint to at least partially correct the misalignment of the axis of rotation. The method can include inserting the prosthesis into a medial compartment of the knee joint and moving the axis to a less varus condition, or inserting the prosthesis into a lateral compartment of the knee joint and moving the axis to a less valgus condition.

The above features and advantages, along with other features and advantages of the present invention are readily apparent from the following detailed description of the best mode for carrying out the invention when taken in connection with the accompanying drawings.

DETAILED DESCRIPTION OF THE PREFERRED EMBODIMENT(S)

The prosthesis according to the present invention is a unicompartmental device suitable for minimally invasive, surgical implantation into a knee compartment without requiring bone resection. The knee compartment is defined by the space between a femoral condyle and the respective tibial plateau, in which a portion of the natural meniscus is ordinarily located. By effectively replacing worn articular material, the prosthesis of the present invention restores the normal joint alignment and provides a smooth bearing surface against which the femoral condyle can articulate. Degeneration of the femoral anatomy is significantly reduced because the conforming femoral surface of the prosthesis accommodates the complex shape of the femoral condyle in extension as well as in flexion. Further, it essentially eliminates articulation of the femoral condyle against the tibial plateau, thereby preventing further degradation of the tibial surface. By occupying the joint space and retensioning the collateral ligaments, the prosthesis according to the present invention improves joint stability and restores the limb to a more normal mechanical alignment.

By the term "unicompartmental" it is meant that each prosthesis according to the present invention is suitable for implantation into but one medial or lateral compartment defined by the space between a femoral condyle and its associated tibial plateau. In other words, the present prosthesis is not a bicompartmental prosthesis which, in one rigid device, could be inserted into both of the two femoral condyle/tibial plateau compartments. In many, if not most, cases a prosthesis will be inserted into one compartment only, either the medial or lateral compartment. Most often, it will be the medial compartment as the meniscus and associated articular surfaces in the medial compartment are most subject to wear and damage. Additionally, it is possible to insert two separate prostheses into the medial and lateral compartments of the same knee, or to use two such prostheses that are mechanically, but non-rigidly, linked. Advantageously, the prosthesis according to the present invention functions to at least partially correct misalignment in the knee axis of rotation due to disease. More specifically, when placed in the medial compartment, the prosthesis moves the knee axis 300 (see FIG. 11) into a less varus, more valgus condition (typically 0-5° valgus). Likewise, when placed in the lateral compartment, the prosthesis moves the knee axis 300 into a less valgus condition.

The prosthesis according to the present invention is preferably translatable but self-centering. By "translatable" it is meant that during natural articulation of the knee joint the prosthesis is allowed to move or change its position, such that articulation of the knee results in a modest amount of lateral/medial and anterior/posterior translation of the prosthesis relative to the tibial plateau. Thus, the present prosthesis preferably is devoid of means of physical attachment which limit its movement, for example, screws, mating ridges and depressions, porous areas to accommodate tissue regrowth, and the like.

The femoral condyle has two major anterior/posterior radii such that, when the knee is in full extension, one radius position is in contact with the tibial plateau while, during flexion, another portion of the femoral condyle is in contact with the tibial plateau. In addition, the femur rotates with respect to the tibia during flexion, thereby changing the orientation of the femoral anatomy to the tibial plateau. The term "self-centering" means that upon translation from a first position to a second position during knee articulation, the prosthesis of the present invention will return to substantially its original position as the articulation of the knee joint is reversed and the original knee position is reached. Thus, the prosthesis will not progressively "creep" towards one side of the compartment in which it is located, but rather the prosthesis is shaped such that the contour of the prosthesis and the natural articulation of the knee exerts a restoring force on the free-floating prosthesis. The angle of attack of the femoral condyle and/or tibial plateau bearing surfaces against the prosthesis will ensure that the prosthesis reversibly translates during articulation, maintaining the prosthesis, on average, in the same location for any given degree of knee articulation.

The centered, rest position, of the prosthesis is usually determined when the knee is in extension and there is maximum contact between the femoral condyle and the prosthesis. In order to ensure the ability of the prosthesis to "self-center," adequate tension of the cruciate and collateral ligaments should be maintained.

While the prosthesis according to the present invention is shown and described herein as being implanted in a knee joint, it is understood that the prosthesis could be utilized in joints other than the knee, such as the hip, shoulder, wrist, ankle, or elbow.

Turning now to FIGS. 1-4, an implantable knee prosthesis 100 according to the present invention is illustrated. Prosthesis 100 includes a body 102 having a generally elliptical shape in plan and including a bottom, or tibial, surface 104 and an opposite top, or femoral, surface 106. Bottom surface 104 is preferably generally flat and top surface 106 is preferably generally concave. However, it is understood that other contours of top and bottom surfaces 104, 106 are fully contemplated in accordance with the present invention. For example, depending on the condition of the ligaments and other soft tissue structure at the time of surgery and how much stability the knee will require, for a medial compartment implantation top surface 106 typically ranges from generally flat to concave and bottom surface 104 typically ranges from generally flat to convex. For a lateral compartment implantation, top surface 106 can range from generally convex to generally concave and bottom surface 104 typically ranges from generally flat to concave (see FIG. 9). It is also understood that the terms "concave" and "convex" as used herein are not restricted to describing surfaces with a constant radius of curvature, but rather are used to denote the general appearance of the surfaces.

With continued reference to FIGS. 1-4, body 102 further includes a peripheral edge 112 extending between bottom surface 104 and top surface 106 and having a first side 114, a second side 116 opposite first side 114, a first end 118, and a second end 120 opposite first end 118. Maximum elongation in the anterior-posterior and medial-lateral directions of peripheral edge 112 is preferred in order to accommodate a large ROM with deformation rather than motion of prosthesis 100. As shown, edges along the periphery of prosthesis 100 are rounded rather than presenting sharp corners, such as in those devices of U.S. Pat. No. 5,158,574. This rounded periphery is desired due to the fact that prosthesis 100 is preferably allowed to move within the joint cavity. Periphery 108 of body 102 is on average of greater thickness than a central portion 110 of body 102 (see FIG. 1), and preferably body 102 generally has a negative meniscus shape when viewed from the side (see FIG. 3) or in a section across body 102 in an anterior-posterior direction from first end 118 to second end 120 (see, for example, FIG. 6). Furthermore, in a preferred embodiment, a section across the body in a medial-lateral direction from first side 114 to second side 116 has a thickness at a periphery of first side 114 which is larger on average than a thickness at a periphery of second side 116 (see, for example, FIG. 7).

In the embodiment depicted herein, second side 116 of body 102 has an indentation 124 formed therein. When implanted in a patient's knee compartment (see FIG. 11), indentation 124 will be proximate to the tibial spine and can preferably be designed to vary in shape from patient to patient as necessary due to the great range of variability of human anatomy. With indentation 124, prosthesis 100 is generally kidney-shaped when viewed in plan, with the shape resembling a distorted ellipse. Of course, indentation 124 is not required, and other variations of body configuration are fully contemplated according to the present invention. Accordingly, it is understood that the term "generally elliptical" is intended to include all construction methods which yield a generally planar shape which is longer in one direction than in the transverse direction and has rounded corners, and that prosthesis 100 is not otherwise limited to any particular shape.

Figure 6:
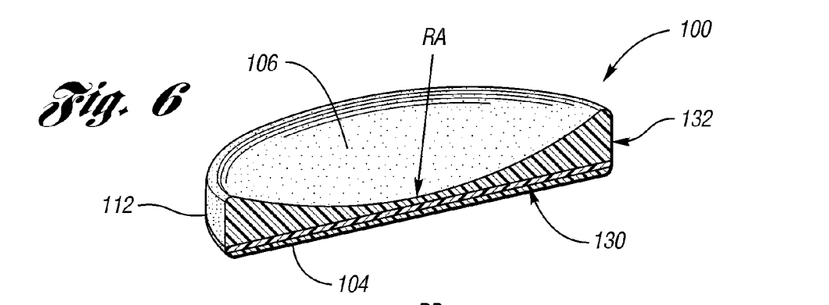
FIG. 6 is a perspective, cross-sectional view of the prosthesis taken along line A-A of FIG. 5.
Figure 7:
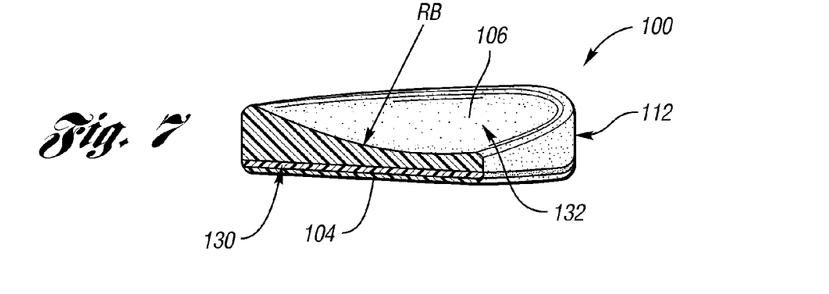
FIG. 7 is a perspective, cross-sectional view of the prosthesis taken along line B-B of FIG. 5.

As shown in FIGS. 1-4 and 8-10 as well as the cross-sectional views of FIGS. 6-7, prosthesis 100 includes a first, supporting portion 130 and a second, coating portion 132. Supporting portion 130 and coating portion 132 have differing material properties as described below to provide a structured, durable prosthesis 100 that is also deformable.

Figure 9:
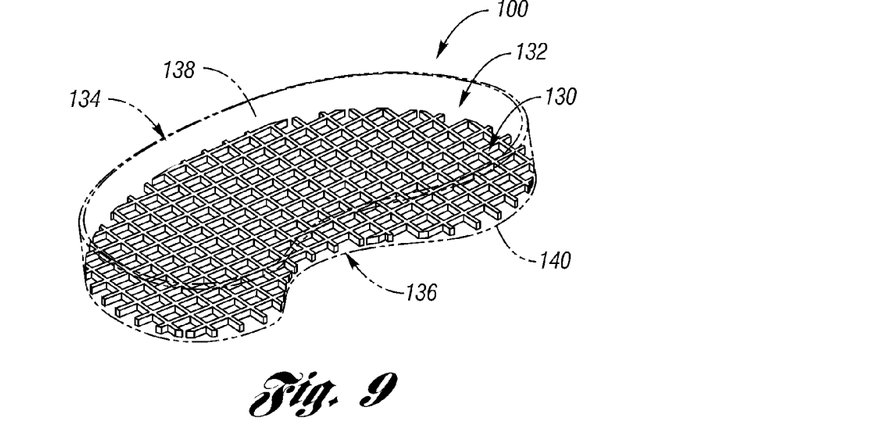
FIG. 9 is a perspective view of the prosthesis according to the present invention showing a supporting portion having a lattice-type configuration.
Figure 10:
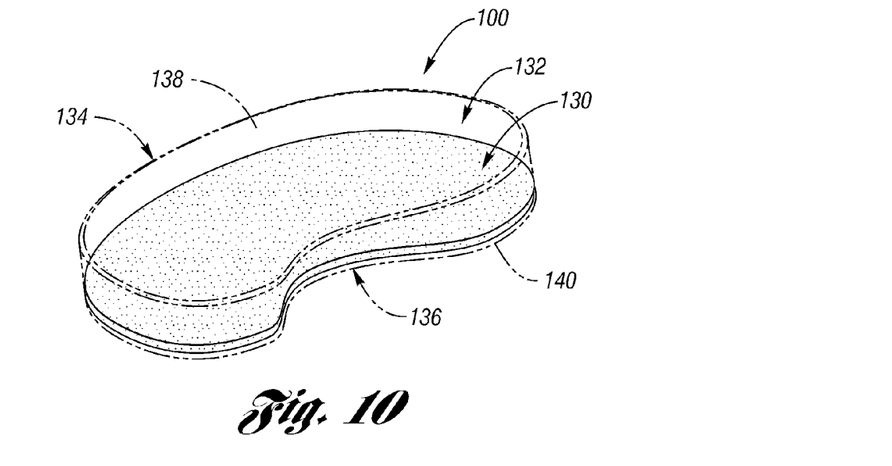
FIG. 10 is a perspective view of the prosthesis according to the present invention showing a supporting portion of solid construction.

Supporting portion 130 serves as a rigid "backbone" for prosthesis 100. In contrast to current collagen-based designs which are absorbed over time, supporting portion 130 of prosthesis 100 of the present invention retains a permanent function throughout the life of prosthesis 100. Supporting portion 130 can be solid as best shown in FIG. 10, or can be porous, such as the lattice-type structure depicted in FIG. 9. Of course, other porous, semi-porous, or solid configurations of supporting portion 130 are also fully contemplated in accordance with the present invention. Supporting portion 130 can be generally planar as shown in FIGS. 1-4, 6-7, and 9-10, or can be contoured as shown, for example, in FIG. 9. The embodiment of prosthesis 100 shown in FIG. 9 is typically intended for a lateral compartment implantation, and therefore supporting portion 130 includes a generally convex upper surface 134 and a generally concave lower surface 136. However, it is understood that other contours of supporting portion 130, such as a generally concave upper surface 134 or a generally convex lower surface 136, are fully contemplated according to the present invention. The thickness of supporting portion 130 can be constant as shown herein, or alternatively could vary. On average, the thickness of supporting portion 130 is selected to be less than the overall prosthesis thickness determined to be required for the patient, but is not otherwise restricted to any particular dimension.

Supporting portion 130 comprises a relatively high modulus material which is strong and stiff enough to maintain prosthesis dimensions and shape. Materials suitable for the construction of supporting portion 130 include, for example, metals such as steel or titanium, metal alloys such as those described in U.S. Pat. Nos. 3,989,517; 5,368,659; and 5,618,359 (LiquidMetal, Inc.), ceramics, hydrogels, and reinforced and non-reinforced thermoset or thermoplastic polymers. Supporting portion 130 need not be made only of a single material, but composite structures may be used. The hardness of the material for supporting portion 130 should be sufficient to allow prosthesis 100 to span defects in the tibia or femur without substantially deforming into the defects, allowing for the provision of recessed or non-contacting areas of the prosthesis to encourage articular regeneration.

Figure 8:
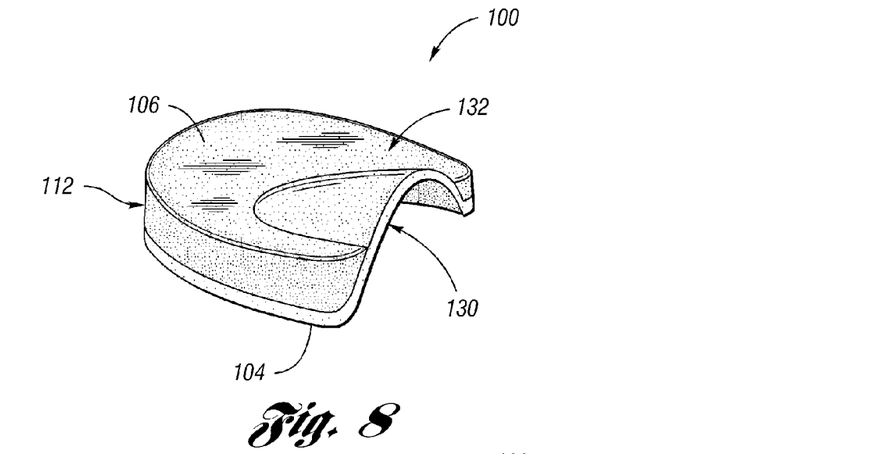
FIG. 8 is a perspective view of another embodiment of the prosthesis according to the present invention.

In contrast, coating portion 132 comprises a lower modulus material as compared with supporting portion 130, where coating portion 132 is at least slightly deformable in order to absorb load energy. Coating portion 132 preferably includes both a top layer 138 and a bottom layer 140 which enclose supporting portion 130 in a sandwich-like manner, and which can be constructed to totally surround supporting portion 130. However, as best shown in FIG. 8, coating portion 132 may only partially, and not completely, cover supporting portion 130. Bottom layer 140 preferably has thickness of about 0.1 to 1.0 mm, any may be of constant or varying thickness. Furthermore, it is contemplated that only one of top layer 138 or bottom layer 140 may be utilized, such as the embodiment depicted in FIG. 8. More particularly, FIG. 8 illustrates an embodiment of prosthesis 100 wherein bottom layer 140 has been eliminated, such that bottom surface 136 of supporting portion 130 becomes the bottom, or tibial, surface 104 of prosthesis 100.

As depicted herein, top layer 138 of coating portion 132 is typically thicker than bottom layer 140, and likewise can have a constant or variable thickness. As described above, for a medial compartment implantation, top surface 106 of prosthesis 100 is preferably generally concave, and bottom surface 104 of prosthesis 100 is preferably generally flat. The relative thicknesses of supporting portion 130 and coating portion 132 are chosen to allow for some deformability of prosthesis 100, but are not otherwise limited to any specific configuration.

Preferred material choices for coating portion 132 include hydrogel formulations such as polyacrylic acid (PAA) hydrogels, photo-crosslinked polyethylene oxide (PEO) hydrogels, polyvinyl pyrrolidone (PVP) hydrogels, and PVA based hydrogels as described in U.S. Pat. Nos. 6,962,701; 6,231,605; and 5,981,826. Due to their low modulus of elasticity, hydrogels can absorb a significant amount of energy but cannot transfer that energy without significant deformation of shape. Hydrogels are typically limited in application since they have relatively low "burst" resistance and thus usually must be contained on all sides and be of relatively small size and depth. While the above patents describe the unsupported use of hydrogel materials in joints as cartilage replacements, the use of hydrogels in coating portion 132 of prosthesis 100 of the present invention is supported by the relatively more rigid supporting portion 130 such that the deformation of the hydrogel is constrained. With this configuration, coating portion 132 can advantageously assume more of the true function of the meniscus by deforming with minimal displacement under loading stresses, and prosthesis 100 can treat much larger areas of defects that the hydrogel alone. Furthermore, the structure provided by supporting portion 130 allows the hydrogel to be used in lesser thickness which increases its lifespan and durability.

As an alternative to hydrogel materials, other biologically considerate materials can be used to construct coating portion 132 as long as they are compliant to load deformation, are load bearing and load absorbing, and have a low coefficient of friction. As such, other suitable material choices include elastomeric polymers such as nylon, silicone, polyurethane, polypropylene, polyester, or the like, optionally fiber-reinforced, thermoplastic urethanes, hyaluronan derivatives or composites, or other viscous-elastic, hydrophilic, or hydroscopic materials. Composites could be used to construct coating portion 132, where the areas of coating portion 132 expected to have the most wear due to either high stress or greater movement relative to the femoral condyle or tibial plateau may be made of stronger, more abrasion resistant material than the remainder of coating portion 132. For example, limited compression in the weight bearing extension area may be desired. Materials capable of containing living cells can be utilized, and surface properties can be modified to better promote surface lubricity, such as via selective component add-ins or selective radiation cross-linking. Still further, a surface application on coating portion 132 can be utilized, such as for the reduction of friction of prosthesis 100.

Bonding of the supporting portion 130 and the coating portion 132 is accomplished via mechanical and/or chemical techniques, either through holes of supporting portion 130 when a porous supporting portion 130 (FIG. 9) is used, or via surface treatments (e.g., etching) of supporting portion 130 when a solid supporting portion 130 (FIG. 10) is utilized. The coating portion 132 material can be overmolded onto, around, and through supporting portion 130 to form the completed prosthesis 100. When preparing a hydrogel material, a freeze-thaw method can be employed as in known in the art (see U.S. Pat. Nos. 6,962,701; 6,231,605; and 5,981,826). The insertion of the hydrogel may be accomplished in the more compact, "dry" form to facilitate insertion with subsequent hydration in the joint. An isostatic pressure chamber, such as an autoclave, can be used to consolidate the hydrogel in the hydrated state, or chemical substitution can be used to form the hydrogel with a non-aqueous medium and exchange the medium with water after formation.

The hard yet deformable nature of prosthesis 100 of the present invention advantageously accommodates both the conformal fit that a matched component offers in an ideal knee and the mismatch that often occurs when one introduces patient specific kinematic ROM such as femoral roll-back and differing amounts of medial pivot or lateral pivot-shift mechanisms into the "real world" equation. The intact meniscus carries 50-90% of the total load in a medial knee joint, and prosthesis 100 of the present invention accomplishes load absorption through deformation as well as movement. Importantly, prosthesis 100 can mimic the conformal meniscal behavior not just in extension, but throughout the range of motion, thereby reducing wear and load on the remaining articular surfaces and increasing patient comfort. Furthermore, due to its compressibility, prosthesis 100 according to the present invention has an adjustable thickness which acts to compensate for the inconsistency of the extension gap to the flexion gap during knee rotation.

In accordance with the present invention, prosthesis 100 may be manufactured so as to substantially contain, or have deposited thereon, a biologically or pharmaceutically active material such as, for example, one that promotes tissue regrowth, retards tissue degeneration, or decreases inflammation. The active material can be provided in the form of an application on coating portion 132, or can be contained within coating portion 132 or supporting portion 130 in the form of a solid, liquid, gel, paste, or soft polymer material. Such active materials may be designed to be delivered at once or in a timed-release manner.

One purpose of the prosthesis 100 of the present invention is to bridge areas of the femoral condyle and/or tibial plateau which have been damaged or have experienced tissue degeneration, without substantially deforming into the defects. If a soft and/or low modulus elastomer or thermoplastic were to be used for the entire prosthesis as in prior art devices, not only would the load not be concentrated on healthy tissue, but damaged areas would also be subjected to static and dynamic loading and wear, thereby decreasing the opportunity for the body's natural regenerative capability to function. Under such circumstances, active materials will be rapidly dissipated and newly regenerated articular cartilage not having the necessary density or cohesiveness to withstand wear will quickly be eroded away. Rather than substantially deforming as in prior art devices to distribute a load relatively equally on the mating femoral and tibial surfaces, prosthesis 100 according to the present invention does not necessarily spread the load uniformly, but rather may redistribute the load to healthy tissue, spanning areas of imperfection and allowing inflamed, diseased, or other damaged areas to regenerate. Moreover, as regeneration proceeds, the regenerating tissue will assume a shape dictated by the shape of prosthesis 100. Growth under these circumstances has the greatest potential for dense, ordered cartilage most closely replicating the original surface.

Prosthesis 100 is preferably allowed to be mobile, accommodating a wide variety of patient kinematic types. However, the forces required to deform the prosthesis 100 must be balanced with the forces attempting to move the prosthesis 100 from its position on the tibia. These forces are present regardless of whether the prosthesis 100 is fixed to the tibia or not. Thus, while prosthesis 100 is described herein as being mobile, it is fully contemplated that prosthesis 100 could easily be converted to an embodiment in which its movement is constrained by mechanical or chemical attachment to the tibia, femur, the surrounding synovial membrane, meniscal remnants, or the like. In this embodiment, the intent is not necessarily to fix prosthesis 100 in one permanent location, but rather to limit its motion in order to balance motion of prosthesis 100 with deformation and load absorption and also as a means of preventing dislocation. Attached applications, with a conformal meniscal shape on the femoral surface, could be used as a fixed tibial device where bottom layer 140 is designed to attach to the tibial plateau, possibly after some bone resection. In this way, the top layer 138 of coating portion 132 could act as a completely functional, normal meniscus.

Much study has been dedicated to determine if any relationship exists in the normal human anatomy that would allow one to define the required dimensions of the prosthesis for proper fit and function based on a single, easy to establish, measurable anatomic landmark. Based on a study of over 100 MRI's and 75 X-rays of human subjects ranging from 15 to 87 years of age, a relationship was established between the anteroposterior radius of the most distal portion of the femoral condyle and the dimensions which control the geometric form of the prosthesis. The database revealed a range of femoral anteroposterior radii from 32 mm to 48 mm. However, it is known that the worldwide range is much larger because of genetic differences in the human anatomy.

Figure 1:
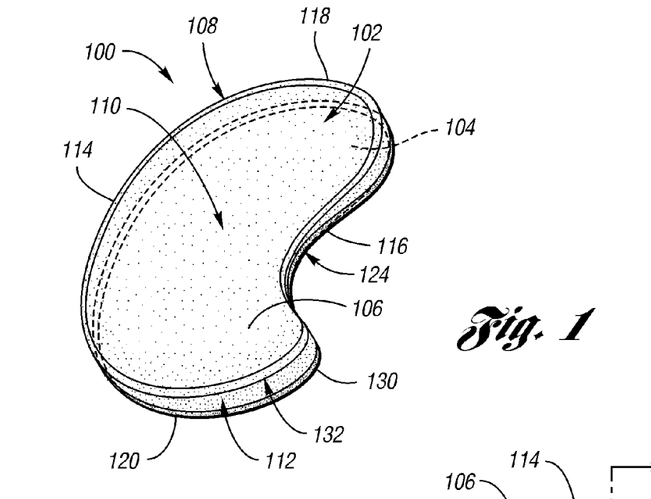
FIG. 1 is a perspective view illustrating an implantable knee prosthesis according to the present invention.
Figure 2:
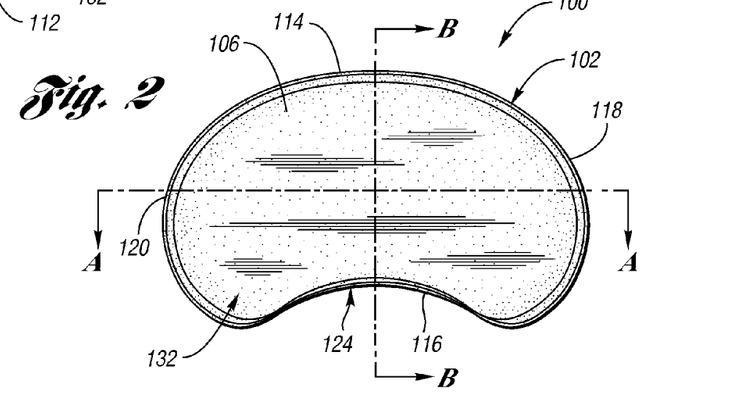
FIG. 2 is a top plan view of the prosthesis of FIG. 1.
Figure 3:
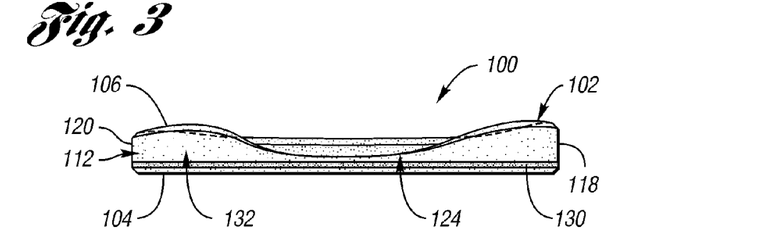
FIG. 3 is a side elevational view of the prosthesis of FIG. 1.
Figure 4:
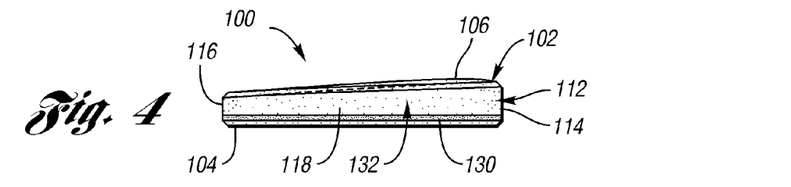
FIG. 4 is an end elevational view of the prosthesis of FIG. 1.
Figure 5:
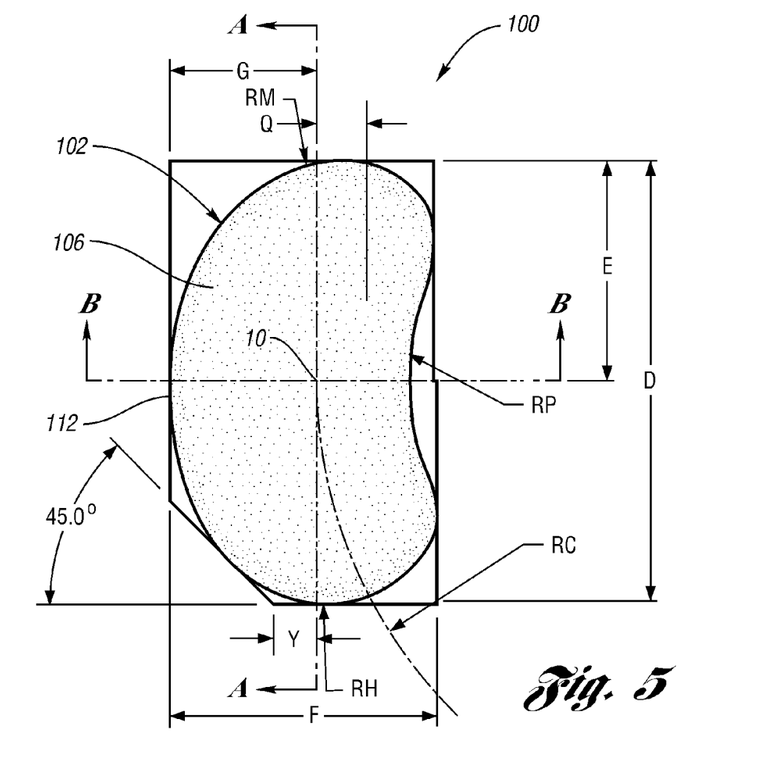
FIG. 5 is a top plan view of the prosthesis according to the present invention with reference to a coordinate system.

With reference now to FIG. 5, a preferred method of construction of the prosthesis 100 of the present invention aligns the apex of a femoral radius with the Coordinate System Origin (CSO) 10. The apex of a tibial surface is also generally aligned in both the anterior/posterior with the CSO 10, but is separated vertically from the CSO 10 to create the part thickness. The generally elliptical shape of peripheral edge 112 is then located with respect to the CSO 10. In general, the CSO 10 of the prosthesis 100 is located at the center of the ellipse. It has been found that a suitable size for body 102 is defined by a minor axis of the ellipse F (defined by first side 114 and second side 116) and a major axis D (defined by first end 118 and second end 120) which are related by a ratio ranging from F=0.25D to 1.5D. Similar ratios can be established for all of the controlling dimensions of the part such that the shape in plan, femoral surface geometry, and tibial surface geometry for a normal tibial anatomy can generally be defined by one physical anterior/posterior measurement of the patient's tibial anatomy. The appropriate thickness of the prosthesis 100 can be determined by measuring the amount of joint space between the femoral and tibial surface when a minor amount of valgus (heels out, knees in) is applied to the knee.

Referring to FIGS. 5-7, the preferred relationship between femoral radius RA (see FIG. 6) to other joint dimensions (femoral radius is the driving relationship to all other dimensions) is as follows:

Medial-lateral radius RB=0.25RA to 1.0RA (see FIG. 7)
Curve of anterior half of femoral radius RC=0.5RA to 2.0RA, posterior half is straight
Length D=0.6RA to 1.4RA
Posterior half E=0.1RA to 0.75RA
Width F=0.25RA to 1.5RA
Width from part center to medial edge G=0.096RA to 0.48RA
Anterior plan radius RH=0.16RA to 0.64RA
Posterior plan radius RM=0.16RA to 0.64RA
Radius along lateral spine area RP=0.1RA to 2.0RA
Width from part center to lateral edge Q=−0.32RA to 0.32RA
Location of transition from anterior radius to medial radius Y=−0.32RA to 0.32RA (A negative value means that a dimension may extend to an opposite side of section line A-A).

The actual shape of the prosthesis 100 may be tailored to the individual. Individuals with high varus or valgus deformation due to wear, degeneration, or disease may require a prosthesis which is of considerably greater thickness over the portions where wear is most advanced. In youthful patients, where trauma-induced damage rather than severe wear or degeneration has occurred, differences in prosthesis thickness will be more moderate.

The axis of rotation of the tibia on the femur is 90 degrees to the path of the tibial plateau against the femoral condyle. The two tibial plateaus (medial and lateral) are not in the same plane with each other but do act in a relatively constant radius to their respective femoral condyles. In other words, although the symmetry of the femoral side of the prosthesis may be matched with the femoral condyle while the leg is in full extension, the rotation of the tibial plateau against the femoral condyle is along a constant axis of rotation (90 degrees to the axis of rotation), thus the angularity of the axis of symmetry of the femoral condyle relative to the axis of symmetry of the tibial plateau is not parallel but at some acute angle. Also, the axis of symmetry of the tibial plateau is not parallel to the path of rotation of the tibia relative to the femur, but also at some mildly acute angle. Thus, the true orientation of the prosthesis, regardless of the relative orientations of symmetry of the tibial side to the femoral side is 90 degrees to the true axis of rotation as described in Hollister et al., "The Axes of Rotation of the Knee," Clin Orthopaedics and Rel Res 290, pp. 259-268, 1993, herein incorporated by reference. Any localized positions of higher loads are self-limiting due to the ability of the prosthesis to translate both rotationally and laterally which mimics the true motion of the natural meniscus as described by Hollister.

During the load bearing portion of the gait cycle, or stance phase, flexion at the knee does not typically exceed 35°. Thus, the highest compressive loads in the knee occur with the knee substantially extended. The outer contours of the prosthesis are therefore preferably designed to substantially mate with the corresponding tibial and femoral surfaces when the knee is in full extension so that the high compressive loads can be distributed over large surface areas. The contact areas between the femoral condyle and the femoral surface of the prosthesis and between the tibial plateau and the tibial surface of the prosthesis are substantially equivalent during extension. However, because the contour of the femoral surface is more concave, the femoral condyle determines the position of the prosthesis on the surface of the tibial plateau in extension.

As the knee is flexed, the mating along the tibial surface is substantially maintained. However, the contoured mating surfaces of the femoral condyle and femoral surfaces of the prosthesis of the present invention can become increasingly dissimilar when the joint articulates. As the knee is flexed, there is a relative external rotation and posterior translation of the femur with respect to the tibia. Thus, the contour angle of the femur becomes more in-line with the contour angle of the tibia in flexion. This can cause relative lateral or rotational movement, in the tibial plane, between the femoral condyle and the femoral surface of the prosthesis. The forces generated by the increasingly different geometry creates a rotational moment in the tibial plane which is resisted along the mating tibial surfaces and which also results in a restoring force tending to correctly locate the prosthesis along the femoral condyle. Thus, the prosthesis is self-centering to the femoral condyle, in part as a result of the conformity between the femoral condyle and the femoral surface of the prosthesis.

By changing the femoral surface of the prosthesis, it is possible to reduce the rotational moment induced during flexion by the mismatch between the femoral surface of the prosthesis and the femoral condyle. A preferred method to accommodate this motion is to have a less acute alignment between the femoral and tibial axes of symmetry posterior to the anterior/posterior midline, thereby reducing the mismatch between the two axes in flexion. This angle is preferably 0° and can range from +/−15°. Anterior to the midline, the femoral contour is bent around a radius RC that is tangent to the posterior section of the sweep plane at the most distal point of the femoral anterior/posterior radius RA. This femoral surface geometry is essentially a compromise between the different extension and flexion alignments of the femoral and tibial axes of symmetry.

Because the prosthesis 100 according to the present invention preferably has no physical method of attachment, the generally concave femoral surface serves to locate the prosthesis through all ranges of motion. Of course, it is understood that proper tensioning of the collateral ligaments is also important to maintain positioning of the prosthesis. By the very nature of the ability to adjust for the lost articular material through the thickness of the prosthesis, the thickness adjustment substantially eliminates the need for a functional meniscus as a bearing surface in a severely (Grade III or IV) degenerated knee. In these instances, the femoral surface of the prosthesis resides significantly above the meniscal edge, and the meniscus is completely unloaded.

The prosthesis according to the present invention also increases the translational stability of the knee. The conforming shape of the femoral surface limits excessive anterior to posterior translation of the femur. As a result, this prosthesis possibly eliminates the need for ACL reconstruction in the older patient.

Generally speaking, each knee presents a different geometry of the respective femoral condyles and tibial plateaus. Even with respect to the right and left knees of a single individual, although bilateral symmetry dictates that the left and right knee components should be mirror images, this is often only an approximation. Thus, the shape of the affected femoral condyle and tibial plateau (while discussed herein in the singular, more than one pair of condyle(s)/plateau(s) may be involved), will have to be ascertained to determine the correct geometry of the prosthesis 100 for a given patient.

To implant a prosthesis that possesses the characteristics required by the subject invention, the patient's knee joint may be examined by a non-invasive imaging procedure capable of generating sufficient information such that one appropriately sized and shaped device may be selected. A variety of non-invasive imaging devices may be suitable, for example magnetic resonance imaging (MRI), X-ray devices and the like.

Two methods of non-invasive imaging for selection of a suitable prosthesis 100 are preferred. In the first method, MRI or other non-invasive imaging scans, optionally coupled with exterior measurements of the dimensions of the relevant tibial and femoral portions including the surface of the articular cartilage of the tibia and femur, may be used to establish a library of prostheses whose size and geometry differ according to the age and size of the patient, the patient's genetic make-up, and the like. A limited number of "standard" prostheses are then made to meet the requirements of a generic population of patients. In this first method, a non-invasive imaging scan, such as an X-ray or MRI, together with knowledge of the patient's genetic make-up, general body type, extent of the disease, degeneration, or trauma and the like, will enable the surgeon to select a prosthesis 100 of the correct size and shape from the library for the patient.

In a second method, each patient receives one or more prostheses that are custom tailored for the individual by producing a contour plot of the femoral and tibial mating surfaces and the size of the meniscal cavity. Such a contour plot may be constructed from imaging data (i.e., X-ray or MRI data) by a suitable computer program. From the contour plot, the correct surface geometry of the prosthesis 100 is determined from the shape of the respective tibial plateau and femoral condyle and the orientation between the two surfaces in extension. In general, the shapes just mentioned also include the articular cartilage which is typically maintained substantially intact.

In accordance with the present invention, it has been discovered that the amount of varus deformity is the primary, non-invasive method for determining the necessary thickness of the prosthesis 100 required for proper functioning. Viewing a weight bearing anteroposterior X-ray, a cut and paste of the line drawn through the femoral condyles and repositioned to put them once again parallel to the tibial plateaus will yield a measurement for the approximate thickness of the prosthesis. However, typically the proper thickness of the prosthesis is determined intra-operatively.

Insertion of the prosthesis 100 of the present invention is typically done via a 3 cm to 5 cm medial parapatella incision. The prosthesis 100 is introduced by arthroscopically assisted implantation, generally limited to extensive clean-up of existing damaged tissue, e.g., torn or particulate natural meniscus damage, osteophyte resection, etc. The natural meniscus may be maintained in position or may be wholly or partially removed, depending upon its condition. Under ordinary circumstances, pieces of the natural meniscus which have been torn away are removed, and damaged areas may be trimmed as necessary. In somewhat rarer instances, the entire portion of the meniscus residing in the meniscal cavity may be removed or is not present. No bone resection or mechanical fixation of the prosthesis 100 is required. Only osteophytes which interfere with the prosthesis placement or with proper collateral ligament alignment are removed.

Prosthesis 100 may also be used in conjunction with ACL or PCL repair, tibial osteotomy or articular surfacing procedures such as cartilage transplantations or abrasion anthroplasty. Following insertion of the prosthesis, X-ray, fluoroscopy, or MRI may be used to assess the correct positioning of the prosthesis both intraoperatively as well as postoperatively. Since the surgical procedures used are not severe, and also not irreversible, an unsuitable prosthesis may be readily removed and replaced, either with a different prosthesis from the library, or by a custom prosthesis.

Prosthesis 100 of the present invention is preferably pre-loaded in a compressed state during implantation. Thus, if the joint is temporarily unloaded during periods of exercise, the expandability of the prosthesis of the present invention advantageously allows the prosthesis to maintain contact with both condylar and tibial surfaces throughout the ROM.

Figure 11:
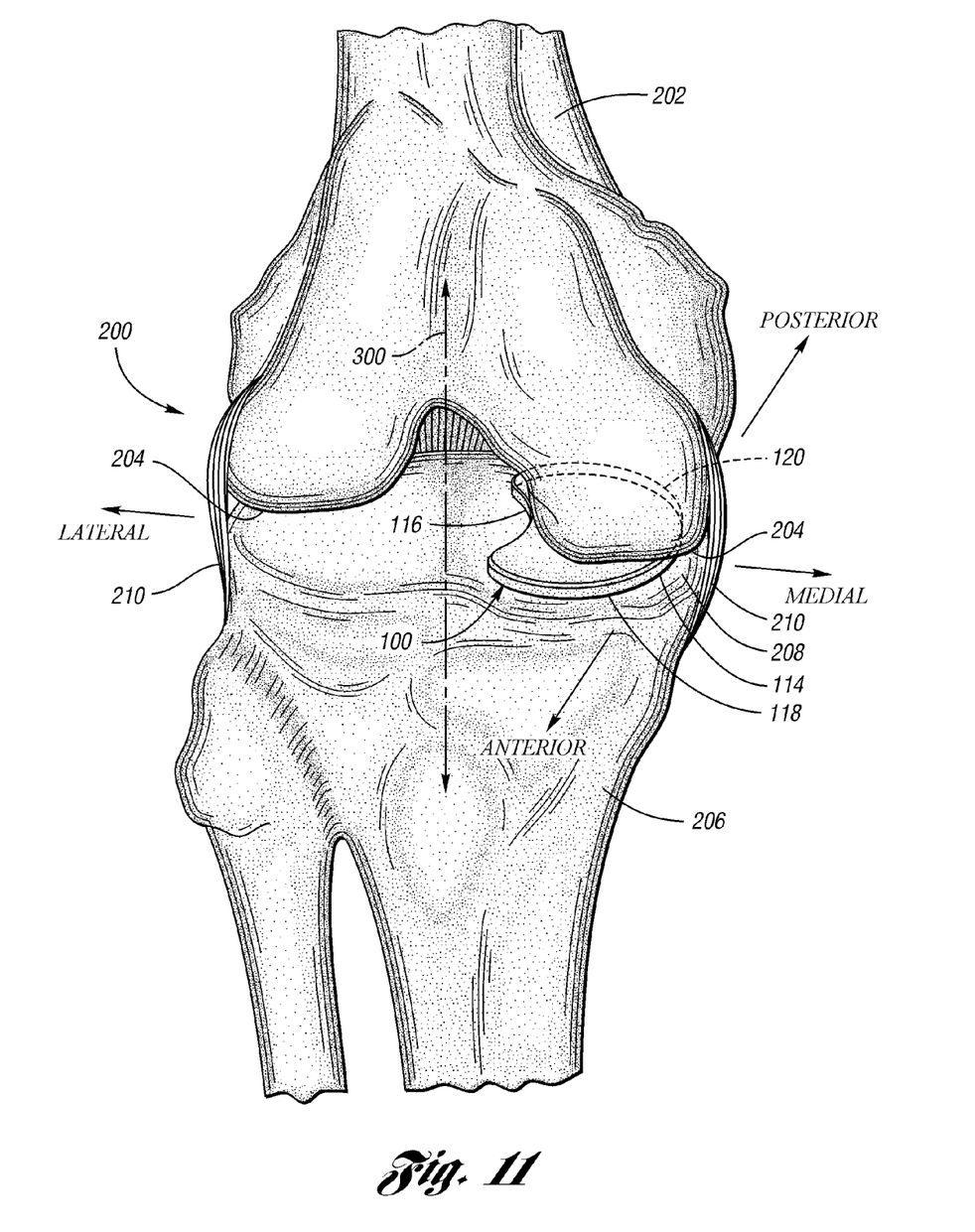
FIG. 11 illustrates an exemplary placement of the prosthesis according to the present invention in a knee joint.

FIG. 11 illustrates prosthesis 100 positioned in a right knee joint 200 between a femur 202, including the femoral condyles 204, and a tibia 206 including the tibial plateau 208. The femur 202 and tibia 206 include interconnecting collateral ligaments 210. FIG. 11 illustrates the position of first side 114, second side 116, first end 118, and second end 120 of prosthesis 100 when inserted in the medial compartment of a patient' right knee joint 200. Of course, prosthesis 100 according to the present invention may just as easily be implanted in a lateral compartment or in the left knee of a patient.

One preferred surgical procedure which may be used to implant the prosthesis 100 according to the present invention can be described by the following steps:

1. Verify preoperative indications:
    a. Valgus determination of <5° with erect anterior/posterior X-ray;
    b. Medial compartment disease only. Some lateral spurs may be present; and
    c. Pre-operative sizing via medial/lateral template measurement of anterior/posterior X-ray.
2. Standard Arthroscopy surgical prep:
    a. Infiltrate knee with Lidocaine/Marcaine and Epinephrine.
3. Arthroscopy:
    a. Inspect lateral patello-femoral compartments for integrity, some mild arthosis is acceptable;
    b. Removal of medial meniscus toward the rim along the anterior, medial and posterior portions;
    c. Initial arthroscopic osteophyte removal via ⅛" osteotome and burr to allow for valgus positioning of the knee;
    d. Complete the removal (to the rim) of the posterior and posterior-lateral meniscus; and
    e. Confirm sizing of the prosthesis by measuring distance from resected meniscus to remaining anterior meniscus.
4. Medial parapatellar arthrotomy (mid-patella to tibial joint line).
5. Complete removal of visible osteophytes along the medial femoral condyle.
6. Insert thickness gauge and size for thickness of prosthesis.
7. Insert trial component:
    a. Flex knee to approximately 50+ degrees to fully expose the distal portion of the femoral condyle;
    b. Insert trial component; and
    c. While applying insertion pressure, apply valgus stress to the tibia and "stretch-extend" the tibia over the trial component.
8. Check for proper sizing with "true lateral" and anterior/posterior fluoroscope images of the knee while in extension:
    a. Ideally, the prosthesis should be within 1 mm of the anterior/posterior boundaries of the tibial plateau and superimposed over the medial boundary.
9. Remove trial component and flush joint with saline.
10. Insert the appropriate prosthesis.
11. Confirm proper placement and sizing with fluoroscopic images as with trial component.
12. Maintain leg in extension and close wound after insertion of a Hemovac drain.
13. Place leg in immobilizer prior to patient transfer.

While embodiments of the invention have been illustrated and described, it is not intended that these embodiments illustrate and describe all possible forms of the invention. The words used in the specification are words of description rather than limitation, and it is understood that various changes may be made without departing from the spirit and scope of the invention.

What is claimed is:

1. A unicompartmental knee prosthesis for implantation into a knee joint compartment between a femoral condyle and its corresponding tibial plateau, the prosthesis comprising:
    a body having a generally elliptical shape in plan, the body including opposed top and bottom surfaces and having a material thickness at a part center (CSO) thereof, the prosthesis free of any means of fixation to the knee joint and configured to be translatable within the knee joint compartment, the body including a supporting portion and a coating portion, the coating portion including a top layer attached to an upper surface of the supporting portion and a bottom layer attached to a lower surface of the supporting portion, wherein the top layer is on average of greater thickness than the bottom layer, the supporting portion having at least one surface at least partially disposed within an interior of the body and the coating portion having at least one surface disposed on an exterior of the body, wherein the supporting portion is constructed from a higher modulus material than the coating portion such that the body is at least slightly deformable.

2. The prosthesis according to claim 1, wherein the top layer has a constant thickness.

3. The prosthesis according to claim 1, wherein the top layer has a variable thickness.

4. The prosthesis according to claim 1, wherein the bottom layer has a thickness of about 0.1 to 1.0 mm.

5. The prosthesis according to claim 1, wherein the bottom layer has a constant thickness.

6. The prosthesis according to claim 1, wherein the bottom layer has a variable thickness.

7. The prosthesis according to claim 1, wherein the coating portion surrounds the supporting portion.

8. The prosthesis according to claim 1, wherein the supporting portion is solid.

9. The prosthesis according to claim 1, wherein the supporting portion is porous.

10. The prosthesis according to claim 9, wherein the supporting portion has a lattice configuration.

11. The prosthesis according to claim 1, wherein the supporting portion includes an upper surface which is generally flat.

12. The prosthesis according to claim 1, wherein the supporting portion includes an upper surface which is generally concave.

13. The prosthesis according to claim 1, wherein the supporting portion includes an upper surface which is generally convex.

14. The prosthesis according to claim 1, wherein the supporting portion includes a lower surface which is generally flat.

15. The prosthesis according to claim 1, wherein the supporting portion includes a lower surface which is generally concave.

16. The prosthesis according to claim 1, wherein the coating portion is constructed at least partially from a material selected from the group consisting of hydrogels, reinforced and non-reinforced elastomeric polymers, thermoplastic urethanes, hyaluronan derivatives or composites, viscous-elastic materials, or composites thereof.

17. The prosthesis according to claim 16, wherein said hydrogels include polyacrylic acid (PAA) hydrogels, photo-crosslininked polyethylene oxide (PLO) hydrogels, polyvinyl pyrrolidone (PYP) hydrogels, and PVA based hydrogels.

18. The prosthesis according to claim 1, wherein the supporting portion is constructed at least partially of a material selected from the group consisting of ceramics, metals, metal alloys, hydrogels, reinforced and non-reinforced thermoset or thermoplastic polymers, or composites thereof.

19. The prosthesis according to claim 1, wherein the body is constructed at least partially of a material capable of containing living cells.

20. The prosthesis according to claim 1, further comprising a surface application associated with the coating portion.

21. The prosthesis according to claim 1, wherein the body includes an active material associated therewith.

22. The prosthesis according to claim 1, wherein the top surface of the body is generally concave.

23. The prosthesis according to claim 1, wherein the top surface of the body is generally convex.

24. The prosthesis according to claim 1, wherein the bottom surface of the body is generally flat.

25. The prosthesis according to claim 1, wherein the bottom surface of the body is generally concave.

26. The prosthesis according to claim 1, further including a peripheral edge extending between the top and bottom surfaces of the body and having a first side, a second side opposite the first side, a first end, and a second end opposite the first end.

27. The prosthesis according to claim 26, wherein a first dimension D is defined by the first end and the second end, and a second dimension F is defined by the first side and the second side, wherein the dimension F is from about 0.25D to about 1.5D.

28. The prosthesis according to claim 1, wherein outside edges along a periphery of the body are rounded.

29. The prosthesis according to claim 1, wherein the coating portion is joined to the supporting portion by overmolding the coating portion onto the supporting portion.

30. The prosthesis according to claim 1, wherein the coating portion is joined to the supporting portion by overmolding the coating portion onto the supporting portion.

* * * * *

UNITED STATES PATENT AND TRADEMARK OFFICE
CERTIFICATE OF CORRECTION

PATENT NO. : 7,491,235 B2 Page 1 of 1
APPLICATION NO. : 10/832213
DATED : February 17, 2009
INVENTOR(S) : Barry M. Fell It is certified that error appears in the above-identified patent and that said Letters Patent is hereby corrected as shown below:

Column 16, Line 64, Claim 17:

Delete "(PLO)" and insert -- (PEO) --.

Column 16, Line 65, Claim 17:

Delete "(PYP)" and insert -- (PVP) --.

Column 18, Line 16, Claim 30:

Delete "30. The prosthesis according to claim 1, wherein the coating portion is joined to the supporting portion by overmolding the coating portion onto the supporting portion."

And insert -- 30. The prosthesis according to claim 1, wherein the coating portion is joined to the supporting portion by surface treatment of the supporting portion. --.

Signed and Sealed this

Fourteenth Day of April, 2009

JOHN DOLL
*Acting Director of the United States Patent and Trademark Office*